United States Patent

Rovati et al.

[11] Patent Number: 6,156,335
[45] Date of Patent: Dec. 5, 2000

[54] PREPARATION WITH AN ACRYLIC-BASED, ADHESIVE COPOLYMERIC MATRIX FOR THE TRANSDERMAL DELIVERY OF ESTRADIOL

[75] Inventors: Luigi Rovati; Lucio Rovati; Francesco Makovec, all of Monza, Italy; Günter Cordes, Leichlingen; Wilfried Fischer, Bad Tölz, both of Germany

[73] Assignee: Rotta Research Laboratorium S.p.A., Monza, Italy

[21] Appl. No.: 08/244,132

[22] PCT Filed: Nov. 24, 1992

[86] PCT No.: PCT/EP92/02704

§ 371 Date: Jul. 15, 1994

§ 102(e) Date: Jul. 15, 1994

[87] PCT Pub. No.: WO93/10772

PCT Pub. Date: Jun. 10, 1993

[30] Foreign Application Priority Data

Nov. 25, 1991 [IT] Italy ................................ TO91A0907

[51] Int. Cl.[7] ................................................. A61F 13/02
[52] U.S. Cl. ................................ 424/448; 424/449
[58] Field of Search ................................ 424/448, 449

[56] References Cited

U.S. PATENT DOCUMENTS 4,906,475  3/1990  Kim ........................................... 424/449
4,994,267  2/1991  Sablotsky ................................. 424/78

Primary Examiner—Thurman K. Page
Assistant Examiner—Isis Ghali
Attorney, Agent, or Firm—Pitney, Hardin, Kipp & Szuch, LLP

[57] ABSTRACT

The invention is represented by a transdermal medicated patch for the extended release of 17β-estradiol to the skin. The transdermal patch is formed by an outer covering, a matrix containing from 1% to 5% (w/w) 17β-estradiol, and a protective liner which is removed before use. The matrix is formed of pressure-sensitive adhesive acrylic copolymers, in which the active ingredient is dissolved or dispersed. The acrylic copolymers are obtained by radical copolymerization of 2-ethylhexyl acrylate, methyl acrylate, acrylic acid, vinyl acetate, hydroxyethyl acrylate or a mixture thereof. Optionally quantities of less than 0.5% (w/w) of other substances may be added.

8 Claims, 1 Drawing Sheet

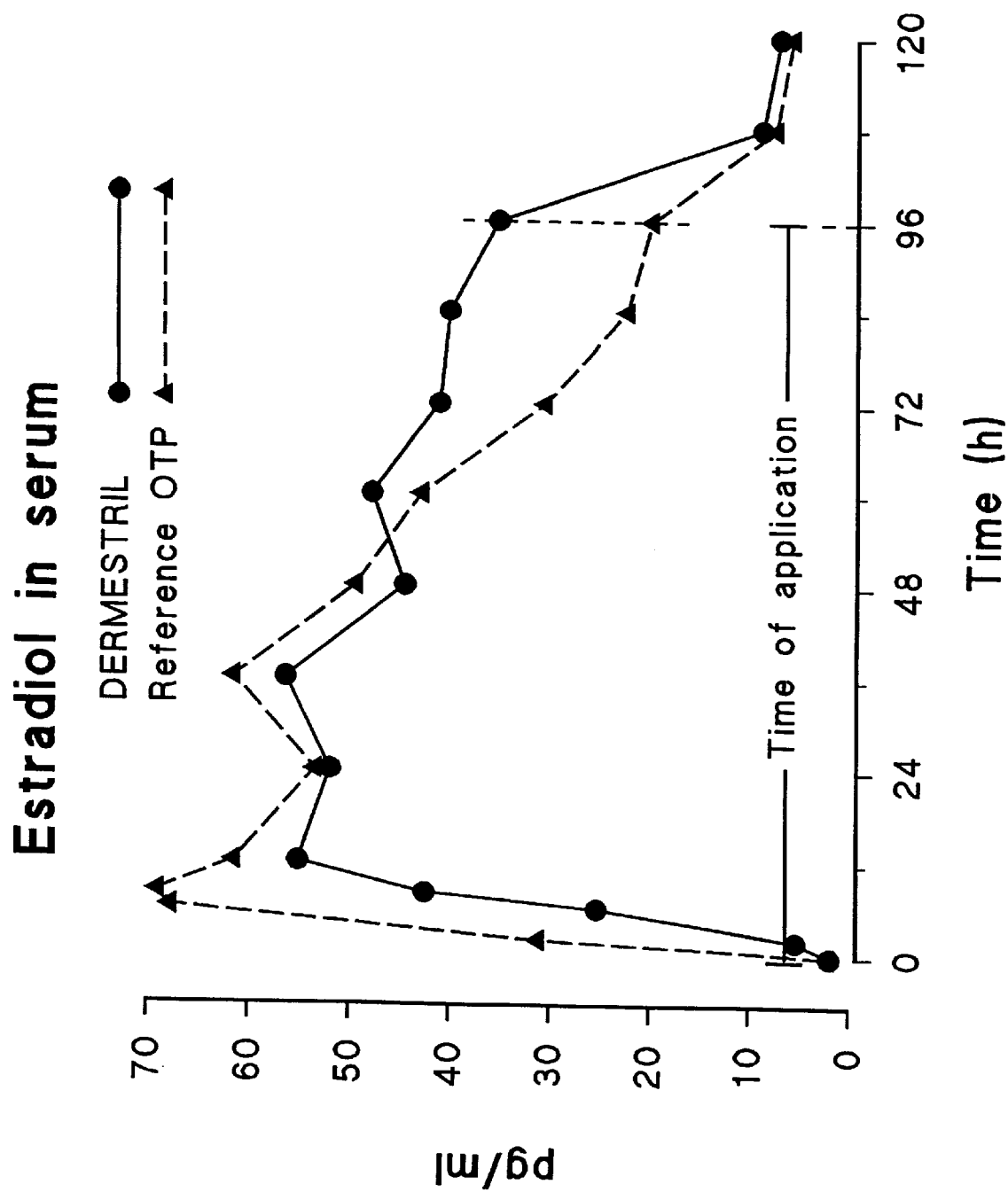

PREPARATION WITH AN ACRYLIC-BASED, ADHESIVE COPOLYMERIC MATRIX FOR THE TRANSDERMAL DELIVERY OF ESTRADIOL

This application is a 371 of PCT/EP92/02704 filed Nov. 24, 1992.

BACKGROUND OF THE INVENTION

1. Field of the Invention

The invention relates to pharmaceutical delivery systems and more particularly to preparations for transdermal administration of estradiol.

2. Brief Description of Related Art

Introduction

Ovarian secretion of 17β-estradiol is lacking in postmenopausal women. In many women this physiological phenomenon induces progressive hypotrophy of the urogenital system as well as characteristic vasomotor symptoms, often followed by osteoporosis affecting particularly the vertebral column.

These climacteric symptoms can be prevented by an exogenous estrogen-based hormone replacement therapy. However, the oral administration of 17β-estradiol (hereinafter referred to as "estradiol") has problems, since the hormone is modified in the intestine and in the liver and produces high blood levels of its metabolites, such as estradiol sulfate, estrone and estrone sulfate which may accumulate in the organism, if the administration is prolonged. One of the undesired effects of the oral administration of estradiol is the increased synthesis by the liver of proteins, including the substrate of renin, with a possible consequent increase in arterial pressure.

The oral route can be bypassed by the transdermal administration of estradiol, which delivers the active ingredient directly into the systemic circulation. However, the diffusion of estradiol through the skin is difficult. To improve it, a special transdermal systems must be developed that can enhance the absorption of estradiol, such as an especially designed, estradiol containing, pressure sensitive adhesive patch, i.e. an Estradiol Transdermal Patch (hereinafter referred to as "OTP").

The OTP represents a considerable therapeutic progress, over the conventional oral administration, since it avoids the "first pass effect" and delivers estradiol directly into the systemic circulation in quantities comparable to those which are physiologically produced by the ovaries.

A widely used OTP is represented by a reservoir in which estradiol is dissolved in ethanol gelatinised with, for example, hydroxypropyl cellulose. The reservoir is contained by a membrane, through which estradiol diffuses to the skin. In this system the membrane becomes the diffusion-rate limiting component of the OTP, as it is the case of an OTP already on the market.

Various patents have been applied for in connection with OTPs provided with diffusion-rate limiting membranes and the use of solvents such as ethanol, alone or in mixture, for dissolving or dispersing estradiol in the drug reservoir, and for improving its absorption through the skin. Thus, for example, GB patent 2158 355 describes the use of a combination of propylene glycol and glycerol in variable ratios; U.S. Pat. No. 4,658,343 described the use of polyethylene glycol monolaurate as agent for improving the skin-penetration of estradiol ("enhancer"), and EP patent 0 147 146 describes the use of methanol for the same purpose.

The transdermal systems based on a diffusion-rate limiting membranes involve various problems. For instance any small hole in the membrane causes inevitably the breakdown of the whole transdermal system.

These systems often require the use of absorption enhancers, which ultimately act by disrupting the intercellular connections of the superficial layers of the skin. This effect increase the permeability of the skin to the active ingredient but often causes skin irritation or sensitisation. The absorption enhancers may also be absorbed through the skin causing unwanted systemic side effects.

In general the systems with diffusion-rate limiting membranes do not allow to achieve constant release rates of the active ingredient, which is disadvantageous since usually the therapeutic treatments require that the active ingredient is released over a prolonged period of time.

Another possible structure of transdermal systems is that of the so-called "monolithic" systems. In these systems the active ingredient is dissolved or dispersed in a "matrix", which becomes the drug reservoir and contains also the pressure sensitive adhesives which assure the adhesion of the transdermal system to the skin. In these systems the release of the active ingredient from the matrix takes place by diffusion, which is driven by the chemical potential of the active ingredient resulting from the concentration gradient and the thermodynamic properties of the components of the matrix.

Many patents have recently been published on OTP based on matrix systems.

Thus, for example, EP patent 0 379 045 describes an OTP in which the system contains 2% estradiol dispersed in a matrix constituted by an acrylic polymer, an ethylene/vinyl acetate copolymer, gums and adhesives. Lecithin, butylene diglycol and propylene diglycol are used as absorption enhancers.

EP patent 0 371 496 describes an OTP in which estradiol is dispersed in a matrix constituted by acrylic polymers, vinyl acetate, gums and silicone, containing also various enhancers such as oleic acid, ethanol and glycols.

JP patent 02 196 714 described the use of a matrix constituted by a copolymer based on 2-ethylhexyl acrylate and vinyl pyrrolidone, and absorption enhancers consisting of lactic esters formed by $C_1$–$C_{20}$ alcohols.

EP patent 0 341 202 describes the use of methyl pyrrolidone and eucalyptol as enhancers.

A last example is EP-A-88 394.3, which describes a transdermal patch containing as enhancers polysorbate 80, polyoxyethylene ethers and aliphatic alcohols with high molecular weight.

The use of enhancers to improve the absorption of estradiol through the skin is clear from the quoted patent literature.

In order to avoid the drawbacks connected with the enhancers (skin irritation, systemic side effects) the absorption of the active ingredient can be improved by increasing its thermodynamic activity in the matrix, for example by increasing its concentration. This, however, often leads to supersaturated matrices due to the limited solubility of the active ingredients. In order to stabilise the supersaturation, additives must be included in the matrix (cfr. for example, DE-C-3 933 460). Nevertheless the systems remain in metastable conditions and the incorporated active ingredients may crystallise during time, decreasing their thermodynamic activity, which is the driving force for diffusion through the skin. The physical stability of these systems is therefore not predictable. The crystallisation of the active ingredients may also change the adhesive properties of the transdermal patch, jeopardising the adhesion of the matrix to the skin and the reliable drug absorption.

The matrix of "monolithic" transdermal patches must therefore comply with several prerequisites. In fact the active ingredient must be provided by a notable thermodynamic potential and nevertheless it must be stable in time. Since the matrix contains also the pressure sensitive adhesives which stick the patch to the skin, it must have good "tack" properties.

Nevertheless the patch must be easily removable from the skin after use, and during this procedure the matrix must remain attached to the outer covering and not to the skin. The adhesives must not "creep", because in this case the patch would stick to the container. As already pointed out, the matrix should not contain absorption enhancers, in order to prevent skin irritation or sensitisation. In addition, obviously, all the components of the matrix must be well tolerated by the skin, even after repeated and prolonged applications of the patches.

SUMMARY OF THE INVENTION

Several formulations were investigated in order to optimize the matrix of the OTP described in this invention. Most formulations were based on acrylic copolymers, to which different substances were added in order to improve the adhesive quality of the matrix, for example hydroabiethylalochol, glycerylester of hydrated collophonium, pentaester of hydrated collophonium, methylester of partially hydrated collophonium, or α-methylstyrol/styrol copolymers. All these formulations had to be discarded because of crystallisation of the active ingredient or impairment of its release rate.

Based on this experience a monolithic matrix was developed which represents a definite improvement over the present state of the art, since it eliminates or reduces to a minimum the main disadvantages of the transdermal patches known up to now and previously described. In fact the new invention provides a system for the transdermal administration of estradiol which is well tolerated, is stable, is effective, prevents the crystallisation of the active ingredient in the matrix, ensures adequate and extended levels of the active ingredient in blood, and has very good tack and adhesive properties.

BRIEF DESCRIPTION OF THE DRAWING

The accompanying drawing is a graph showing a comparison of the averages of serum estradiol levels in 20 postmenopausal women during the application for 96 hours of an OTP of the invention (Dermestril) or a reference OTP.

DETAILED DESCRIPTION OF THE PREFERRED EMBODIMENTS OF THE INVENTION

According to the invention the above mentioned features were provided by a transdermal patch for the extended release of 17β-estradiol onto the skin consisting of:
a) an outer covering (backing foil);
b) pressure-sensitive adhesive copolymers constituting the matrix in which the active ingredient is dissolved or dispersed (drug reservoir);
c) a protective liner which is removed at the time of use;

The invention describes a new transdermal patch for the extended release of estradiol to the skin, in which the active ingredient is dissolved or dispersed in a suitable pressure-sensitive adhesive copolymeric matrix, and which surprisingly avoids the need of substances to improve the absorption of the drug through the skin (enhancers), or of supersaturated solutions of the active ingredient, thus preventing problems of skin compatibility and of stability of the whole system.

A specific embodiment concerns a transdermal medicated patch which is characterised in that the components of the adhesive copolymers are obtained by radical polymerization of 2-ethylhexyl acrylate, methyl acrylate, acrylic acid, vinyl acetate, hydroxyethyl acrylate or mixtures thereof, possibly with quantities of less than 0.5% (w/w) of other additives in the adhesive copolymers.

A specific embodiment of the invention concerns a transdermal medicated patch in which the adhesive copolymers of the matrix are obtained by radical polymerization of (w/w of the matrix) about 50% to 70% (preferably 55% to 65% and especially 61% to 64%) 2-ethylhexyl acrylate, about 20% to 40% (preferably 24% to 32% and especially 25% to 28%) methyl acrylate, about 2% to 8% (preferably 3% to 5% and especially 4% to 5%) acrylic acid, about 2% to 10% (preferably 3% to 7% and especially 4% to 5%) vinyl acetate, and about 0.5% to 3% (preferably 0.7% to 1.5% and especially about 1%) hydroxyethyl acrylate.

Small quantities of less than 0.5% of other substances may also be used to improve the adhesive properties and the strength of the matrix.

According to the invention no cross-linker is used in the adhesive copolymer, such as titanium acetylacetonate, as it is suggested by the prior art, in order to avoid creeping of the adhesives onto the removable protective liner and therefore sticking of the patch to its container. The problem of creeping is surprisingly avoided in the invention by using the described copolymers obtained by radical polymerization.

The OTP according to the invention is characterized by a content of 17β-estradiol from 1% to 5%, preferably 2.0% to 2.5%, (w/w) of the weight of the adhesive copolymers.

A specific embodiment of the invention concerns a transdermal patch which contains about 4 mg 17β-estradiol per 18 to 20 cm$^2$ of patch area.

A specific embodiment of the invention of the transdermal patch comprises an outer covering of suitable protective materials, which forms the external backing foil of the patch and is constituted by a foil of thin, flexible and water-impermeable material, preferably selected from the group of polyester, polyurethane, polyethylene and/or polyvinyl chloride. Finally, the transdermal patch according to the invention comprises a removable protective liner, preferably constituted by a foil of paper or polyester which is preferably silicone-coated on one or both sides and that is easily removed at the time of use without impairing the transdermal patch.

According to the additional embodiment of the invention, a process is described for the production of a transdermal patch for the extended release of 17β-estradiol to the skin, which is characterized in that pressure-sensitive adhesive copolymers containing 17β-estradiol as active ingredient are spread onto a removable protective liner and then covered by another liner which becomes the outer covering.

Alternatively the pressure-sensitive adhesive copolymers containing 17β-estradiol are spread on a water-impermeable foil which becomes the outer covering, and are then covered by the protected liner.

Still alternatively the pressure-sensitive adhesive copolymers containing 17β-estradiol are spread on an intermediate liner (usually a siliconized paper sheet) and then covered by the foil of the outer covering to which the copolymers adhere firmly. In the final manufacturing process the intermediate liner is removed and substituted by the protective liner.

According to a predetermined embodiment of the claimed process the transdermal patch can be produced as follows:

- the pressure-sensitive adhesive copolymers are dissolved in an organic solvent (adhesive mixture);
- 17β-estradiol, dissolved or dispersed in an organic solvent or in a mixture of solvents, is dissolved or dispersed in the adhesive mixture by stirring, at a concentration from 1% to 5% (w/w) of the dry weight of the pressure-sensitive adhesive copolymers;
- the obtained mixture is concentrated by evaporation of some of the solvents and then spread onto the removable protective liner, preferably constituted by a foil of paper or polyester which is silicone-coated on one or both sides; alternatively the mixture is spread onto the foil of the outer covering, constituted by water-impermeable materials preferably selected from the group of polyester, polyurethane, polyethylene and/or polyvinyl chloride; still alternatively the mixture is spread on an intermediate liner, preferably constituted by a sheet of paper, preferably siliconized on one or on both sides;
- the solvent is evaporated at a temperature from 30° to 80° C. with or without applying a vacuum;
- a foil of thin, flexible and water-impermeable material constituting the outer covering is applied, or, alternatively the final protective liner is applied or alternatively the intermediate liner is removed and replaced by the final protective liner, according one of the three procedures outlined above as examples;
- the produced composite medicated foil is cut into portions of appropriate shape and surface, such that they contain the required quantity of the active ingredient suitable for the therapeutic use, and in this way the final transdermal patches are obtained.

The appropriate qualitative-quantitative selection of the acrylic components of the final copolymer obtained by radical polymerization, i.e. 2-ethylhexyl acrylate, acrylic acid and hydroxyethyl acrylate, and of vinyl acetate which acts as solvent for the active ingredient, is suitable for a transdermal system for the extended release of estradiol which is stable in time and does not give rise to crystallisation of the active ingredient in the matrix.

Moreover, as will be described below, the serum levels of estradiol in menopausal patients obtained after having applied the transdermal patch to their skin, are more constant during the application time than during the application of a patch provided with a diffusion-rate limiting membrane and ethanol as enhanced. Surprisingly the extent of absorption after the application of the invented OTP was similar to that of the enhanced system.

EXAMPLE 1

(Production of a transdermal patch containing 4 mg of estradiol)

The production process of the transdermal patch according to the present invention, containing 4 mg of 17β-estradiol as the active ingredient per 18 cm² of patch area (hereinafter referred to as "DERMESTRIL"), is illustrated further by the following, non-limiting example.

An adhesive mixture was prepared dissolving in 3 liters of ethylacetate a mixture of copolymers obtained by radical polymerization of 1038 g 2-ethylhexyl acrylate, 520 g methyl acrylate, 68 g of acrylic acid, 87 g vinyl acetate, and 17 g hydroxyethyl acrylate.

A quantity of 40 g of 17β-estradiol was dissolved or finely suspended in a mixture of solvents constituted by 1 liter of propan-2-ol and 1.5 liters of ethyl acetate. This solution was added, under stirring, to the mixture of copolymers, prepared as described above.

The mixture was stirred until a homogeneous mass was obtained and this was evaporated to produce a mixture with a consistency appropriate for spreading on the appropriate liners. Then the adhesive mixture containing the active ingredient was spread onto a foil of silicone-coated paper or polyester and dried at a temperature between 30° and 80° C. to produce a film of matrix weighing about 98 g/m² (±5%) as the dry weight, corresponding to about 2.2 g of 17β-estradiol per m² of the dry matrix.

Finally, a polyester foil, about 15 μm thick, was stuck on the matrix to form the outer covering of the patch.

Individual circular patches having areas of 18 cm², each containing about 4 mg of the active ingredient were cut from the composite medicated foil to form the final transdermal patch.

In summary, the steps of preparing the estradiol transdermal patch (OTP) according to the present invention consist substantially of:

- adding a solution of a fine suspension of estradiol to a suitable mixture of copolymers of acrylates and vinyl acetate;
- spreading a thin layer of the mixture formed by the dispersion of the active ingredient in the acrylic copolymers on a protective liner of silicone-coated paper or polyester to be removed at the time of use;
- drying the liquid adhesive film formed by the acrylic copolymers and containing estradiol, at a temperature between 30° and 80° C. in order to evaporate the solvent, with or without applying vacuum;
- applying a foil of thin, flexible, water-impermeable material which constitutes the outer covering of the patch;
- cutting the composite medicated foil produced as above described into portions having the desired shape and surface, for example 18 cm² for patches containing 4 mg estradiol;
- alternative procedures are also possible, such as spreading the adhesive mixture onto the outer covering or onto an intermediate liner. The following manufacturing steps are then made in order to produce the appropriate final composite medicated foil.

Release of estradiol in vitro

The release of estradiol from the OTP produced according to the invention ("DERMESTRIL") was tested in vitro with the following procedure.

Discs cut from DERMESTRIL OTP, with surface areas of 6 cm² and containing about 1.33 mg of estradiol, were applied to a support deposited on the base of the dissolution test apparatus according to USP XXII, consisting of a 1 liter glass vessel and a rotating blade.

The distance between the support and the blade, which rotated at a speed of 50 revolutions per minute, was 2.5 cm and the dissolution liquid was constituted by 900 ml of water at 32° C.

Portions of 1 ml of the solution were withdrawn at 2, 4, 6, 8, 12, 24 and 36 hours after the start of the experiment, and the estradiol content was determined by HPLC. The test was repeated 6 times.

The quantities of released estradiol, expressed as milligrams and as percent of the nominal content of estradiol in DERMESTRIL at the various times, are given in table 1.

TABLE 1

Milligrams and percent of estradiol released in the in vitro test

| Time (h) | mg | % of nominal |
|---|---|---|
| 2 | 0.66 | 16.5 |
| 4 | 0.95 | 23.8 |
| 6 | 1.25 | 31.2 |
| 12 | 1.70 | 42.5 |
| 24 | 2.48 | 61.9 |
| 36 | 3.20 | 80.0 |

Table 1 shows that from 6 to 36 hours, the release kinetics is linear and can be expressed by the equation:

$$R = 0.8966 + 0.646 \times h$$

where R=mg of estradiol released and h=time in hours.

Table 1 shows also that about 30% of the estradiol contained in the patch had been released after 6 hours, about 60% after 24 hours and about 80% after 36 hours.

Bioavailability of estradiol from DERMESTRIL

The bioavailability study was carried out in postmenopausal women. DERMESTRIL was compared with an OTP commercially available and characterized by a diffusion rate limiting membrane and containing ethanol as solvent and absorption enhancer (hereinafter called "Reference OTP").

Two DERMESTRIL patches prepared according to the invention, and containing each 4 mg of estradiol per 18 cm$^2$ or two Reference OTPs, also containing 4 mg of estradiol, were applied on the skin of the subjects for a single application of 96 hours.

Studied were 20 subjects and the patches were applied according to a cross-over design, with a suitable wash-out period between the two treatments.

Estradiol in blood serum was determined by a RIA method. The estradiol serum levels expressed in pg/ml are given in the accompanying drawing and in table 2. Table 2 gives also the averages of the maximum concentrations found ($C_{max}$), of the times to the peak ($t_{max}$) and of the area under the concentration/time curve (AUC) in the period 0–96 hours after administration.

Table 2

Estradiol levels in serum at various times after the application of 2 OTPs according to the invention (DERMESTRIL) or of 2 commercial OTPs (Reference OTP), Both, DERMESTRIL and the Reference OTP contain each 4 mg estradiol. Averages and SD of 20 subjects.

| | Estradiol pp/ml ± SD | |
|---|---|---|
| Hours | DERMESTRIL | Reference OTP |
| 0 | 1.96 ± 3.94 | 2.06 ± 3.81 |
| 2 | 5.34 ± 7.87 | 31.13 ± 29.45 |
| 6 | 25.27 ± 34.54 | 67.65 ± 42.57 |
| 8 | 42.46 ± 31.52 | 68.91 ± 25.86 |
| 12 | 55.07 ± 46.51 | 61.35 ± 21.26 |
| 24 | 51.86 ± 28.63 | 53.35 ± 16.76 |
| 36 | 56.28 ± 32.87 | 61.37 ± 23.31 |
| 48 | 44.43 ± 24.13 | 49.34 ± 18.37 |
| 60 | 47.74 ± 30.17 | 42.78 ± 21.19 |
| 72 | 41.02 ± 22.29 | 30.48 ± 15.34 |
| 84 | 40.03 ± 19.87 | 22.33 ± 12.87 |
| 96 | 35.18 ± 19.73 | 19.85 ± 9.16 |
| 108 | 8.80 ± 6.51 | 7.49 ± 5.39 |
| 120 | 7.01 ± 5.91 | 5.76 ± 4.89 |
| $C_{max}$ | 66.18 ± 45.0 | 87.35 ± 29.87 |
| $t_{max}$ | 35.00 ± 19.8 | 18.80 ± 18.99 |
| AUC (0–96 h) | 4286 ± 2409 | 4268 ± 1226 |

From the results given in table 2 it can be concluded that the areas under the concentration/time curves (AUC) do not differ significantly after the two treatments. In fact the AUC(0–96) after DERMESTRIL was 4286±2409 (SD), and after the Reference OTP was 4268±1226 (SD).

This demonstrate that the bioavailability of estradiol from DERMESTRIL is the same as that from Reference OTP, and this is a surprising result because DERMESTRIL does not contain absorption enhancers.

Tolerability by the skin

The skin tolerability to the OTP prepared according to the invention was evaluated on 10 female guinea pigs weighing between 300 and 400 g.

The patches were applied to the previously shaved left scapular region of the animals. An area of patch of 2×2 cm cut from DERMESTRIL and thus containing about 0.89 mg estradiol, was stuck on the shaved skin and left there for about 6 hours. The tolerability of the patch was evaluated by the appearance of erythema or oedema after 24 hours of application, according to the following scores.

| Score | ERYTHEMA | OEDEMA |
|---|---|---|
| 0 | No effect | No effect |
| 1 | Slight | Slight oedema |
| 2 | Moderate | Moderate oedema |
| 3 | Intense | Severe oedema |

The test was repeated using the same scores after 7 days, in order to record a possible sensitization induced by the patch.

The overall sum of the scores related to erythema for the 10 animals was 1 of 30, because only 1 animal out of 10 showed a slight erythema (30 is the maximum score obtainable).

No animal presented oedema.

In the sensitisation challenge carried out after 7 days, no animal had erythema or oedema, demonstrating that the patches were well tolerated and did not induce sensitization under the experimental conditions.

EXAMPLES 2 to 5 AND COMPARATIVE EXAMPLES 1 TO 7

Table 3 summarized the composition of the matrix of Examples 1 to 5 and of the Comparative Examples 1 to 7. The corresponding formulations of the matrix containing the copolymers obtained by radical polymerization of the acrylic compounds are quantitatively listed in table 3. The resulting OTPs were tested for stability and also, in six human subjects, for adhesion and skin compatibility. The results obtained with the eleven formulations are also reported in table 3.

The results clearly show that formulations No. 1 to 4 and particularly No. 1 exhibit the properties required for the matrix of a "monolithic" transdermal patch. Conversely other formulations, which are here listed as Comparative Examples 1 to 7, had disadvantages, for instance discolouration (formulations No. 6 to 10), unacceptable skin compatibility (formulation No. 5), or unacceptable tack properties (formulations No. 6, 7, 9 and 11).

TABLE 3

Percentage of monomers in the acrylic copolymers and other substances in different formulations. Properties of the matrix obtained with these copolymers.

| | Examples | | | | Comparative Examples | | | | | | |
|---|---|---|---|---|---|---|---|---|---|---|---|
| | 2 | 3 | 4 | 5 | 1 | 2 | 3 | 4 | 5 | 6 | 7 |
| Formulation No. | 1 | 2 | 3 | 4 | 5 | 6 | 7 | 8 | 9 | 10 | 11 |
| Substances | | | | | | | | | | | |
| 2-EHA | 62.6 | 61.5 | 63.4 | 57.6 | 66.9 | 62.2 | 63.1 | 64.0 | 59.2 | 56.6 | 64.2 |
| HA | 26.4 | 33.0 | 21.5 | 19.5 | 0.0 | 26.4 | 21.5 | 16.5 | 25.1 | 24.0 | 16.5 |
| VA | 5.6 | 0.0 | 9.8 | 8.9 | 28.0 | 5.6 | 9.8 | 14.0 | 5.3 | 5.1 | 14.0 |
| AA | 4.4 | 5.5 | 3.6 | 3.3 | 0.0 | 4.3 | 3.5 | 2.7 | 4.1 | 3.9 | 2.8 |
| GMA | 0.0 | 0.0 | 0.1 | 0.1 | 0.2 | 0.1 | 0.1 | 0.1 | 0.0 | 0.0 | 0.1 |
| HEA | 1.0 | 0.0 | 1.8 | 1.6 | 5.0 | 1.0 | 1.8 | 2.5 | 1.0 | 0.9 | 2.5 |
| TA. | 0.0 | 0.0 | 0.0 | 0.0 | 0.0 | 0.4 | 0.3 | 0.3 | 0.4 | 0.4 | 0.0 |
| HR | 0.0 | 0.0 | 0.0 | 9.1 | 0.0 | 0.0 | 0.0 | 0.0 | 4.8 | 9.1 | 0.0 |
| Features | | | | | | | | | | | |
| Estrad. solub. | G | G | G | G | G | G | G | G | G | G | G |
| Discoloration | – | – | – | – | – | + | + | + | + | + | – |
| Tack on skin | G | G | M | G | G | B | B | G | B | G | S |
| Skin compat. | G | M | M | M | B | G | G | M | G | M | G |

Legenda: B = Bad; M = Medium; G = Good; S = Too strong; + = Present; – = Absent
Substances:
2-EHA = 2-Ethylhexylacrylate
HA = Methylacrylate
VA = Vinyl acetate
AA = Acrylic acid
GMA = Glycidylmethacrylate
HEA = Hydroxyethylacrylate
TA = Titanium acetylacetonate
HR = Hydrocarbon resin

What is claimed is:

1. A transdermal medicated patch for the extended release of 17β-estradiol to the skin, consisting of pressure-sensitive adhesive copolymers in which the active ingredient is dissolved or dispersed, supported by a water-impermeable foil and covered by a protective liner which is removed at the time of use, wherein the pressure-sensitive adhesive copolymers are obtained by radical copolymerization of

| | |
|---|---|
| 55 to 65 weight % | 2-ethylhexyl acrylate |
| 24 to 32 weight % | methyl acrylate |
| 3 to 5 weight % | acrylic acid |
| 3 to 7 weight % | vinyl acetate and |
| 0.7 to 1.5 weight % | hydroxyethyl acrylate. |

2. A transdermal medicated patch according to claim 1, characterized by a content of 17β-estradiol from 1% to 5% by weight of the adhesive copolymers.

3. A transdermal medicated patch according to claim 1, characterized by a content of about 4 mg 17β-estradiol per 18 to 20 cm² of patch area.

4. A transdermal medicated patch according to claim 1 characterized in that the patch comprises a removable protective liner constituted by a sheet of paper.

5. A transdermal patch according to claim 1, characterized by an outer covering constituted by a foil of a water-impermeable material, selected from the group of polyester, polyurethane, polyethylene and/or polyvinyl chloride materials.

6. A process for the production of a transdermal medicated patch according to claim 1, characterized in that pressure-sensitive adhesive copolymers containing 17β-estradiol as active ingredient are spread onto a removable protective liner and then covered by an outer covering.

7. A process for the production of a transdermal medicated patch according to claim 6,, which comprises:

dissolving pressure-sensitive adhesive copolymers in an organic solvent to form an adhesive mixture;

dissolving - 17β-estradiol, in the adhesive mixture by stirring at a concentration from 1% to 5% by weight of the dry weight of the pressure-sensitive adhesive copolymers; and spreading the solution onto a removable protective liner.

8. A transdermal medicated patch according to claim 1, wherein the pressure-sensitive adhesive copolymers are obtained by radical copolymerization of (w/w or the matrix)

| | |
|---|---|
| 61 to 64% | 2-ethylhexyl acrylate |
| 25 to 28% | methyl acrylate |
| 4 to 5% | acrylic acid |
| 4 to 5% | vinyl acetate and |
| about 1% | hydroxyethyl acrylate. -- |

* * * * *